(12) United States Patent
Mahuna

(10) Patent No.: US 9,651,499 B2
(45) Date of Patent: May 16, 2017

(54) CONFIGURABLE IMAGE TRIGGER FOR A VISION SYSTEM AND METHOD FOR USING THE SAME

(75) Inventor: Tyson Mahuna, Tigard, OR (US)

(73) Assignee: COGNEX CORPORATION, Natick, MA (US)

( * ) Notice: Subject to any disclaimer, the term of this patent is extended or adjusted under 35 U.S.C. 154(b) by 1193 days.

(21) Appl. No.: 13/331,866

(22) Filed: Dec. 20, 2011

(65) Prior Publication Data

US 2013/0155220 A1 Jun. 20, 2013

(51) Int. Cl.
*G01N 21/88* (2006.01)
*G06F 3/0484* (2013.01)

(52) U.S. Cl.
CPC ..... *G01N 21/8851* (2013.01); *G06F 3/04847* (2013.01); *G01N 21/8806* (2013.01); *G01N 2021/8867* (2013.01); *G01N 2021/8887* (2013.01)

(58) Field of Classification Search
CPC .................................................. G01N 21/8851
See application file for complete search history.

(56) References Cited

U.S. PATENT DOCUMENTS

| | | |
|---|---|---|
| 4,214,265 A | 7/1980 | Olesen |
| 4,292,666 A | 9/1981 | Hill et al. |
| 4,384,195 A | 5/1983 | Nosler |
| 4,647,979 A | 3/1987 | Urata |
| 4,679,075 A | 7/1987 | Williams et al. |
| 4,847,772 A | 7/1989 | Michalopoulos et al. |
| 4,916,640 A | 4/1990 | Gasperi |
| 4,962,538 A | 10/1990 | Eppler et al. |
| 4,972,494 A | 11/1990 | White et al. |

(Continued)

FOREIGN PATENT DOCUMENTS

| | | |
|---|---|---|
| DE | 10007985 A1 | 9/2000 |
| DE | 10040563 | 2/2002 |

(Continued)

OTHER PUBLICATIONS

"ADSP-BF533 Blackfin Processor Hardware Reference", Analog Devices Inc.—Media Platforms and Services Group, Preliminary Revision—Part No. 82-002005-01, Mar. 2003.

(Continued)

*Primary Examiner* — James Pontius
(74) *Attorney, Agent, or Firm* — Loginov IP

(57) ABSTRACT

This invention provides a trigger for a vision system that can be set using a user interface that allows the straightforward variation of a plurality of exposed trigger parameters. Illustratively, the vision system includes a triggering mode in which the system keeps acquiring an image of a field of view with respect to objects in relative motion. The system runs user-configurable "trigger logic". When the trigger logic succeeds/passes, the current image or a newly acquired image is then transmitted to the main inspection logic for processing. The trigger logic can be readily configured by a user operating an interface, which can also be used to configure the main inspection process, to trigger the vision system by tools such as presence-absence, edge finding, barcode finding, pattern matching, image thresholding, or any arbitrary combination of tools exposed by the vision system in the interface.

20 Claims, 12 Drawing Sheets

(56) References Cited

U.S. PATENT DOCUMENTS

| | | |
|---|---|---|
| 5,018,213 A | 5/1991 | Sikes |
| 5,040,056 A | 8/1991 | Sager et al. |
| 5,121,201 A | 6/1992 | Seki |
| 5,146,510 A | 9/1992 | Cox et al. |
| 5,164,998 A | 11/1992 | Reinsch et al. |
| 5,177,420 A | 1/1993 | Wada |
| 5,184,217 A | 2/1993 | Doering |
| 5,198,650 A | 3/1993 | Wike et al. |
| 5,210,798 A | 5/1993 | Ekchian et al. |
| 5,233,541 A | 8/1993 | Corwin et al. |
| 5,262,626 A | 11/1993 | Goren et al. |
| 5,271,703 A | 12/1993 | Lindqvist et al. |
| 5,286,960 A | 2/1994 | Longacre et al. |
| 5,298,697 A | 3/1994 | Suzuki et al. |
| 5,317,645 A | 5/1994 | Perozek et al. |
| 5,345,515 A | 9/1994 | Nishi et al. |
| 5,365,596 A | 11/1994 | Dante et al. |
| 5,420,409 A | 5/1995 | Longacre et al. |
| 5,476,010 A | 12/1995 | Fleming et al. |
| 5,481,712 A | 1/1996 | Silver et al. |
| 5,500,732 A | 3/1996 | Ebel et al. |
| 5,562,788 A | 10/1996 | Kitson et al. |
| 5,581,625 A | 12/1996 | Connell et al. |
| 5,687,249 A | 11/1997 | Kato |
| 5,717,834 A | 2/1998 | Werblin et al. |
| 5,734,742 A | 3/1998 | Asaeda |
| 5,742,037 A | 4/1998 | Scola et al. |
| 5,751,831 A | 5/1998 | Ono |
| 5,802,220 A | 9/1998 | Black et al. |
| 5,809,161 A | 9/1998 | Auty et al. |
| 5,825,483 A | 10/1998 | Michael et al. |
| 5,852,669 A | 12/1998 | Eleftheriadis et al. |
| 5,872,354 A | 2/1999 | Hanson |
| 5,917,602 A | 6/1999 | Bonewitz et al. |
| 5,929,418 A | 7/1999 | Ehrhart et al. |
| 5,932,862 A | 8/1999 | Hussey et al. |
| 5,937,096 A | 8/1999 | Kawai |
| 5,942,741 A | 8/1999 | Longacre et al. |
| 5,943,432 A | 8/1999 | Gilmore et al. |
| 5,960,097 A | 9/1999 | Pfeiffer et al. |
| 5,960,125 A | 9/1999 | Michael et al. |
| 5,966,457 A | 10/1999 | Lemelson |
| 6,046,764 A | 4/2000 | Kirby et al. |
| 6,049,619 A | 4/2000 | Anandan et al. |
| 6,061,089 A | 5/2000 | Tonkin et al. |
| 6,061,471 A | 5/2000 | Coleman et al. |
| 6,072,494 A | 6/2000 | Nguyen |
| 6,072,882 A | 6/2000 | White et al. |
| 6,075,882 A | 6/2000 | Mullins et al. |
| 6,078,251 A | 6/2000 | Landt et al. |
| 6,088,467 A | 7/2000 | Sarpeshkar et al. |
| 6,115,480 A | 9/2000 | Washizawa |
| 6,158,661 A | 12/2000 | Chadima et al. |
| 6,160,494 A | 12/2000 | Sodi et al. |
| 6,161,760 A | 12/2000 | Marrs |
| 6,169,535 B1 | 1/2001 | Lee |
| 6,169,600 B1 | 1/2001 | Ludlow |
| 6,173,070 B1 | 1/2001 | Michael et al. |
| 6,175,644 B1 | 1/2001 | Scola et al. |
| 6,175,652 B1 | 1/2001 | Jacobson et al. |
| 6,184,924 B1 | 2/2001 | Schneider et al. |
| 6,215,892 B1 | 4/2001 | Douglass et al. |
| 6,282,462 B1 | 8/2001 | Hopkins |
| 6,285,787 B1 | 9/2001 | Kawachi et al. |
| 6,298,176 B2 | 10/2001 | Longacre et al. |
| 6,301,610 B1 | 10/2001 | Ramser et al. |
| 6,315,201 B1 | 11/2001 | Reichenbach et al. |
| 6,333,993 B1 | 12/2001 | Sakamoto |
| 6,346,966 B1 | 2/2002 | Toh |
| 6,347,762 B1 | 2/2002 | Sims et al. |
| 6,360,003 B1 | 3/2002 | Doi et al. |
| 6,396,517 B1 | 5/2002 | Beck et al. |
| 6,396,949 B1 | 5/2002 | Nichani |
| 6,408,429 B1 | 6/2002 | Marrion et al. |
| 6,446,868 B1 | 9/2002 | Robertson et al. |
| 6,483,935 B1 | 11/2002 | Rostami et al. |
| 6,487,304 B1 | 11/2002 | Szeliski |
| 6,525,810 B1 | 2/2003 | Kipman |
| 6,526,156 B1 | 2/2003 | Black et al. |
| 6,539,107 B1 | 3/2003 | Michael et al. |
| 6,545,705 B1 | 4/2003 | Sigel et al. |
| 6,549,647 B1 | 4/2003 | Skunes et al. |
| 6,573,929 B1 | 6/2003 | Glier et al. |
| 6,580,810 B1 | 6/2003 | Yang et al. |
| 6,587,122 B1 | 7/2003 | King et al. |
| 6,597,381 B1 | 7/2003 | Eskridge et al. |
| 6,608,930 B1 | 8/2003 | Agnihotri et al. |
| 6,618,074 B1 | 9/2003 | Seeley et al. |
| 6,621,571 B1 | 9/2003 | Maeda et al. |
| 6,625,317 B1 | 9/2003 | Gaffin et al. |
| 6,628,805 B1 | 9/2003 | Hansen et al. |
| 6,629,642 B1 | 10/2003 | Swartz et al. |
| 6,646,244 B2 | 11/2003 | Aas et al. |
| 6,668,075 B1 | 12/2003 | Nakamura |
| 6,677,852 B1 | 1/2004 | Landt |
| 6,681,151 B1 | 1/2004 | Weinzimmer et al. |
| 6,714,213 B1 | 3/2004 | Lithicum et al. |
| 6,741,977 B1 | 5/2004 | Nagaya et al. |
| 6,753,876 B2 | 6/2004 | Brooksby et al. |
| 6,761,316 B2 | 7/2004 | Bridgelall |
| 6,766,414 B2 | 7/2004 | Francis |
| 6,774,917 B1 | 8/2004 | Foote et al. |
| 6,816,063 B2 | 11/2004 | Kubler |
| 6,817,982 B2 | 11/2004 | Fritz et al. |
| 6,891,570 B2 | 5/2005 | Tantalo et al. |
| 6,919,793 B2 | 7/2005 | Heinrich |
| 6,944,584 B1 | 9/2005 | Tenney et al. |
| 6,947,151 B2 | 9/2005 | Fujii et al. |
| 6,973,209 B2 | 12/2005 | Tanaka |
| 6,985,827 B2 | 1/2006 | Williams et al. |
| 6,987,528 B1 | 1/2006 | Nagahisa et al. |
| 6,997,556 B2 | 2/2006 | Pfleger |
| 6,999,625 B1 | 2/2006 | Nelson et al. |
| 7,062,071 B2 | 6/2006 | Tsujino et al. |
| 7,066,388 B2 | 6/2006 | He |
| 7,070,099 B2 | 7/2006 | Patel |
| 7,085,401 B2 | 8/2006 | Averbuch et al. |
| 7,088,387 B1 | 8/2006 | Freeman et al. |
| 7,088,846 B2 | 8/2006 | Han et al. |
| 7,097,102 B2 | 8/2006 | Patel et al. |
| 7,175,090 B2 | 2/2007 | Nadabar |
| 7,181,066 B1 | 2/2007 | Wagman |
| 7,219,843 B2 | 5/2007 | Havens et al. |
| 7,227,978 B2 | 6/2007 | Komatsuzaki et al. |
| 7,266,768 B2 | 9/2007 | Ferlitsch et al. |
| 7,271,830 B2 | 9/2007 | Robins et al. |
| 7,274,808 B2 | 9/2007 | Baharav et al. |
| 7,280,685 B2 | 10/2007 | Beardsley et al. |
| 7,303,130 B2 | 12/2007 | Solen et al. |
| 7,516,898 B2 | 4/2009 | Knowles et al. |
| 7,604,174 B2 | 10/2009 | Gerst et al. |
| 7,657,081 B2 | 2/2010 | Blais et al. |
| 7,720,364 B2 | 5/2010 | Scott et al. |
| 7,751,625 B2 | 7/2010 | Ulrich et al. |
| 7,773,801 B2 | 8/2010 | Kanda |
| 7,832,642 B2 | 11/2010 | Sato et al. |
| 7,889,886 B2 | 2/2011 | Matsugu et al. |
| 7,960,004 B2 | 6/2011 | Yee et al. |
| 7,973,663 B2 | 7/2011 | Hall |
| 7,984,854 B2 | 7/2011 | Nadabar |
| 8,108,176 B2 | 1/2012 | Nadabar et al. |
| 8,226,007 B2 | 7/2012 | Berkun |
| 2001/0042789 A1 | 11/2001 | Krichever et al. |
| 2002/0005895 A1 | 1/2002 | Freeman et al. |
| 2002/0099455 A1 | 7/2002 | Ward |
| 2002/0109112 A1 | 8/2002 | Guha et al. |
| 2002/0122582 A1 | 9/2002 | Masuda et al. |
| 2002/0177918 A1 | 11/2002 | Pierel et al. |
| 2002/0181405 A1 | 12/2002 | Ying |
| 2002/0196336 A1 | 12/2002 | Batson et al. |
| 2002/0196342 A1 | 12/2002 | Walker et al. |
| 2003/0062418 A1 | 4/2003 | Barber et al. |
| 2003/0095710 A1 | 5/2003 | Tessadro |
| 2003/0113018 A1 | 6/2003 | Nefian et al. |

(56) References Cited

U.S. PATENT DOCUMENTS

| | | |
|---|---|---|
| 2003/0201328 A1 | 10/2003 | Jam et al. |
| 2003/0227483 A1 | 12/2003 | Schultz et al. |
| 2004/0218806 A1 | 11/2004 | Phillips |
| 2005/0184217 A1 | 8/2005 | Kong et al. |
| 2005/0226490 A1 | 10/2005 | Phillips et al. |
| 2005/0254106 A9 | 11/2005 | Silverbrook et al. |
| 2005/0257646 A1 | 11/2005 | Yeager |
| 2005/0275728 A1 | 12/2005 | Mirtich et al. |
| 2005/0275831 A1 | 12/2005 | Silver |
| 2005/0275833 A1 | 12/2005 | Silver |
| 2005/0275834 A1 | 12/2005 | Silver |
| 2005/0276445 A1 | 12/2005 | Silver et al. |
| 2005/0276459 A1 | 12/2005 | Eames et al. |
| 2005/0276460 A1 | 12/2005 | Silver et al. |
| 2005/0276461 A1 | 12/2005 | Silver et al. |
| 2005/0285743 A1 | 12/2005 | Weber |
| 2006/0043303 A1 | 3/2006 | Safai et al. |
| 2006/0056732 A1 | 3/2006 | Holmes |
| 2006/0146337 A1 | 7/2006 | Marshall et al. |
| 2006/0146377 A1 | 7/2006 | Marshall et al. |
| 2006/0249587 A1 | 11/2006 | Smith |
| 2006/0283952 A1 | 12/2006 | Wang |
| 2007/0009152 A1 | 1/2007 | Kanda |
| 2007/0181692 A1 | 8/2007 | Barkan et al. |
| 2008/0118419 A1 | 5/2008 | Lyublinski et al. |
| 2008/0278584 A1 | 11/2008 | Shih et al. |
| 2008/0309920 A1 | 12/2008 | Silver |
| 2008/0310676 A1 | 12/2008 | Silver |
| 2009/0128627 A1 | 5/2009 | Katsuyama et al. |
| 2009/0158315 A1* | 6/2009 | Bendall .................. H04N 7/185 725/32 |
| 2009/0257621 A1 | 10/2009 | Silver |
| 2009/0273668 A1 | 11/2009 | Mirtich et al. |
| 2010/0241901 A1 | 9/2010 | Jahn et al. |
| 2010/0241981 A1 | 9/2010 | Mirtich et al. |
| 2010/0318936 A1 | 12/2010 | Tremblay et al. |

FOREIGN PATENT DOCUMENTS

| | | |
|---|---|---|
| DE | 10012715 | 5/2014 |
| EP | 0939382 | 9/1999 |
| GB | 2226130 | 6/1990 |
| GB | 2309078 | 7/1997 |
| JP | 60147602 | 8/1985 |
| JP | S62-113002 | 5/1987 |
| JP | H8122016 | 5/1996 |
| JP | 08-313454 | 11/1996 |
| JP | 09-178670 | 7/1997 |
| JP | H9-288060 | 11/1997 |
| JP | 11101689 | 4/1999 |
| JP | 200084495 | 3/2000 |
| JP | 2000-227401 | 8/2000 |
| JP | 2000293694 | 10/2000 |
| JP | 2000322450 | 11/2000 |
| JP | 2001109884 | 4/2001 |
| JP | 2001194323 | 7/2001 |
| JP | 2002-148201 | 5/2002 |
| JP | 2002148205 | 5/2002 |
| JP | 2002-214153 | 7/2002 |
| JP | 2002-288633 | 10/2002 |
| WO | 9609597 | 3/1996 |
| WO | 0215120 | 2/2002 |
| WO | 2005124317 | 12/2005 |
| WO | 2005124709 | 12/2005 |
| WO | 2005050390 | 4/2006 |

OTHER PUBLICATIONS

"Bi-i", AnaLogic Computers Ltd., 2003.
"Bi-i: Bio-inspired Real-Time Very High Speed Image Processing Systems", AnaLogic Computers Ltd., http://www.analogic-computers.com/cgi-bin/phprint21.php, 2004.
"Blackfin Processor Instruction Set Reference", Analog Devices, Inc., Revision 2.0, Part No. 82-000410-14, May 2003.
"CCD/CMOS Sensors Spot Niche Application", PennWell Corporation, Vision System Design—Imaging and Machine Vision Technology, 2004.
"Cellular device processes at ultrafast speeds", VisionSystems Design, Feb. 2003.
"Cognex 3000/4000/5000 Image Processing", Revision 7.4 590-0135 Edge Detection Tool, 1996.
"Cognex 4000/5000 SMD Placement Guidance Package, User's Manual", Release 3.8.00, Chapter 15, 590-6168, 1998.
"Cognex VisionPro", Getting Started—QuickStart Tutorial, Cognex Corporation, 590-6560, Revision 3.5, May 2004, 69-94.
"CV-2100 Series", Keyence America http://www.keyence.com/products/vision/cv_2100_spec.html, High-Speed Digital Machine Vision System, Dec. 29, 2003.
"CVL Vision Tools Guide", Cognex MVS-8000 Series, Chapter 5, Symbol Tool, CVL 5.4, Dec. 1999.
"ICS 100—Intelligent Camera Sensor", SICK Product Information, SICK Industrial Sensors, 6900 West 110th Street, Minneapolis, MN 55438 www.sickusa.com, Jan. 3, 2002.
"LM9630 100 × 128, 580 fps UltraSensitive Monochrome CMOS Image Sensor", National Semiconductor Corp., www.national.com. Rev. 1.0, Jan. 2004.
"Laser Scanning Product Guide", Adaptive Optics Associates—Industrial Products and Systems 90 Coles Road, Blackwood, NJ 08012 (Mar. 2003).
"Matsushita Imagecheckers", NAiS Machine Vision—Matsushita Machine Vision Systems, 2003.
"Matsushita LightPix AE10", NAiS Machine Vision—Matsushita Machine Vision Systems, 2003.
"SmartCapture Tool", Feature Fact Sheet, Visionx Inc., www.visionxinc.com, 2003.
Allen-Bradley, "Bulletin 2803 VIM Vision Input Module", Cat. No. 2803-VIM2, Printed USA, 1991. Submitted in 3 parts.
Allen-Bradley, "Bulletin 5370 CVIM Configurable Vision Input. Module", User Manual Cat. No. 5370-CVIM, 1995. Submitted in 3 parts.
Allen-Bradley, "User's Manual", Bulletin 2803 VIM Vision Input Module, Cat. No. 2803-VIM1, 1987. Submitted in 2 parts.
Apple Computer Inc., Studio Display User's Manual online, retrieved on Nov. 24, 2010, retrieved from the Internet http://manuals.info.apple.com/en/studioDisplay_15inLCDUserManual.pdf, 1998.
Asundi, A. et al., "High-Speed TDI Imaging for Peripheral Inspection", Proc. SPIE vol. 2423, Machine Vision Applications in Industrial Inspection III, Frederick Y. Wu; Stephen S. Wilson; Eds., Mar. 1995, 189-194.
Avalon Vision Solutions, "If accuracy matters in your simplest vision applications Use the Validator", 2006.
Baillard et al., "Automatic Reconstruction of Piecewise Planar Models from Multiple Views", CVPR, vol. 2, No. 2, 1999, 2559.
Baumberg et al., "Learning Flexible Models from Image Sequences", University of Leeds, School of Computer Studies, Research Report Series, Report 93.36, Oct. 1993, pp. 1-13.
Baumer Optronic, "Technishche Daten", www.baumeroptronic.com, Product Brochure, Apr. 2006, 6.
Chang, Dingding et al., "Feature Detection of Moving Images using a Hierarchical Relaxation Method", IEICE Trans. Inf. & Syst., vol. E79-D, Jul. 7, 1996.
Chen, Y. H. , "Computer Vision for General Purpose Visual Inspection: A Fuzzy Logic Approach", Optics and Lasers in Engineering 22, Elsevier Science Limited, vol. 22, No. 3, 1995, pp. 182-192.
Cognex Corporation, "3000/4000/5000 Vision Tools", revision 7.6, 590-0136, Chapter 13, 1996.
Cognex Corporation, "Cognex 3000/4000/5000", Vision Tools, Revision 7.6, 590-0136, Chapter 10 Auto-Focus, 1996.
Cognex Corporation, "Screen shot of the CheckMate GUI Ver 1.6", Jan. 2005.
Cognex Corporation, "Sensorpart FA45 Vision Sensor", Sep. 29, 2006.
Cognex Corporation, "VisionPro Getting Started", Revision 3.2, Chapter 5, 590-6508, copyright 2003.
Cordin Company, "Electronic Imaging Systems", High Speed Imaging Solutions: 200-500 Series Cameras, Aug. 4, 2004.

(56) References Cited

OTHER PUBLICATIONS

Corke, Peter I. et al., "Real Time Industrial Machine Vision", Electrical Engineering Congress Sydney, Australia, CSIRO Division of Manufacturing Technology, 1994.
DeMotte, Donald, "Visual Line Tracking", Application Overview & Issues Machine Vision for Robot Guidance Workshop, May 5, 2004.
Denis, Jolivet, "LabVIEW and IMAQ Vision Builder Provide Automated Visual Test System", Semiconductor: IMAQ Advanced Analysis Toolkit, IMAQ Vision Builder—LabVIEW—National Instruments—XP002356529—URL http://www.ni.com/pdf/csma/us/JNDESWG.pdf, 2001.
Di Mauro, E. C. et al., "Check—a generic and specific industrial inspection tool", IEE Proc.-Vis. Image Signal Process., vol. 143, No. 4, Aug. 27, 1996, pp. 241-249.
Haering, N. et al., "Visual Event Detection", Kluwer Academic Publishers, Chapter 2, Section 8, 2001.
Hunt, Shane C., "Mastering Microsoft PhotoDraw 2000", SYBEX, Inc., San Francisco, May 21, 1999, 400p.
IBM, "Software Controls for Automated Inspection Device Used to Check Interposer Buttons for Defects", IP.com Journal, IP.com Inc., West Henrietts, NY, US, Mar. 27, 2003.
Integrated Design Tools, "High-Speed CMOS Digital Camera", X-Stream Vision User's Manual, 2000.
IO Industries, "High Speed Digital Video Recording Software 4.0", IO industries, Inc.—Ontario, CA, 2002.
Kahn, Phillip, "Building blocks for computer vision systems", IEEE.Expert, vol. 8, No. 6, XP002480004, Dec. 6, 1993, 40-50.
Kim, Zuwhan et al., "Automatic Description of Complex Buildings with Multiple Images", IEEE 0/7695-0813-8/00, 2000, 155-162.
KSV Instruments Ltd., "HiSIS 2002—High Speed Imaging.System", www.ksvltd.fi, Sep. 24, 2004.
Lavision Gmbh, "High Speed CCD/CMOS Camera Systems", Overview of state-of-the-art High Speed Digital Camera Systems—UltraSpeedStar, www.lavision.de, Sep. 24, 2004.
Marsh, R et al., "The application of knowledge based vision to closed-loop control of the injection molding process", SPIE vol. 3164, Faculty of Engineering University of the West of England United Kingdom, 1997, 605-16.
Matrox, "Interactive Windows Imaging Software for Industrial and Scientific Applications", Inspector 4.0—Matrox Imaging, Apr. 15, 2002, 8.
National Instruments, "IMAQVision Builder Tutorial", IMAQ XP-002356530, b, ttp://www.ni.com.'pdf,'manuals/322228c.pdf, Dec. 2000.
Olympus Industrial, "Design Philosophy", i-speed, 2002, 4.
Olympus Industrial, "High Speed, High Quality Imaging Systems", i-speed Product Brochure—Publisher Olympus Industrial, 2002, 16.
Photron USA, "Fastcam PCI", Sep. 24, 2004.
Photron USA, "Fastcam-X 1280 PCI", Sep. 24, 2004.
Photron USA, "Ultima 1024", Sep. 24, 2004.
Photron USA, "Ultima 512", Sep. 24, 2004.
Photron USA, "Ultima APX", Sep. 24, 2004.
Rohr, K., "Incremental Recognition of Pedestrians from Image Sequences", CVPR93, 1993.
RVSI "Smart Camera Reader for Directly Marked Data Matrix Codes", HawkEye 1515 with GUI, 2004.
Siemens AG, "Simatic Machine Vision", Simatic VS 100 Series, www.siemens.com/machine-vision, Apr. 1, 2003.
Stauffer, Chris et al., "Tracking-Based Automatic Object Recognition", Artificial Intelligence Laboratory, Massachusetts Institute of Technology, Cambridge, MA http://www.ai.mit.edu, 2001, pp. 133-134.
Stemmer Imaging GmbH, "Going Multimedia with Common Vision Blox", Product News, www.stemmer-imaging.de, Mar. 3, 2004.
Uno, T. et al., "A Method of Real-Time Recognition of Moving Objects and its Application", Pattern Recognition; Pergamon Press, vol. 8, pp. 201-208, 1976, pp. 201-208.
Vietze, Oliver "Miniaturized Vision Sensors for Process Automation", Jan. 2, 2005.
Vision Solutions, "Captura! Video Event Monitoring Solutions", Epic Vision Solutions, Note: have not been able to locate a date for this reference, Unknown.
West, Perry C., "High Speed, Real-Time Machine Vision", Imagenation and Automated Vision Systems, Inc., 2001.
Whelan, P. et al., "Machine Vision Algorithms in Java", Chapter 1—An Introduction to Machine Vision, Springer-Verlag, XP002480005, 2001.
Wilson, Andrew, "CMOS/CCD sensors spot niche applications", Vision Systems Design, Jun. 2003.
Wright, Anne et al., "Cognachrome Vision System User's Guide", Newton Research Labs, Manual Edition 2.0, Documents Software Version 26.0, Jun. 3, 1996.
Zarandy, A. et al., "Vision Systems Based on the 128X128 Focal Plane Cellular Visual Microprocessor Chips", IEEE, Mar. 2003, III-518—III-521
Zarandy, Akos et al., "Ultra-High Frame Rate Focal Plane Image Sensor and Processor", IEEE Sensors Journal, vol. 2, No. 6, 2002.

\* cited by examiner

CONFIGURABLE IMAGE TRIGGER FOR A VISION SYSTEM AND METHOD FOR USING THE SAME

FIELD OF THE INVENTION

This invention relates to vision systems and more particularly to automated trigger functions in a vision system.

BACKGROUND OF THE INVENTION

Machine vision systems are used in a wide range of manufacturing processes. Among other uses, machine vision is employed to ensure quality and to assist in the constructing various articles and devices. A common use for vision systems in industrial applications is in association with an inspection or assembly location on a moving production line. Images of objects are acquired as they pass under the vision system camera's field of view. Based upon image data acquired, the vision system can decide whether there is a flaw in the object, determine its alignment for further processes, operate a robot manipulator, identify and sort the object into an appropriate bin, or perform other automated tasks.

In a typical implementation, the triggering of image acquisition by the vision system is performed according to an external modality. For example, the drive system for the moving line can include an encoder that triggers after a certain number of pulses that are associated with line movement. Likewise a photoeye/photodetector can be used to sense the presence of an object arriving at the field of view. The camera receives a trigger signal from the photoeye to acquire the image at this time. This approach entails additional hardware and has limited ability to modify the conditions for triggering. Such modifications can be desirable in certain applications—for example, where a photoeye cannot be conveniently mounted near the field of view, or has a disadvantageous view of the object.

Some vision systems provide a native image-triggering mode within the camera assembly. However, even when a system has such a native image triggering mode, that mode is typically very rigid such that if a user desires to apply even a slight change to the trigger mode, the system's software would most likely require a change and/or upgrade. This is because the parameters used to change the image trigger mode are typically not exposed to the user in an interface that he or she can access and control. Even if there are parameters exposed to configure the image trigger mode in available vision systems, those parameters are finite and fixed. The user would not, for example, be able to arbitrarily add a filter to the image trigger.

By way of background and definition, a "trigger event" is generally defined as a circumstance in which the system is instructed to acquire an image for inspection. In the case of an external source, such as a photo eye, a trigger event occurs when the object of interest is sufficiently within its view and the photo eye signals a trigger to the camera to acquire the current image and pass it to inspection by the vision system. In the above-described native-image-triggering camera assembly, and as described further below, a trigger event involving an "internal" trigger can entail an acquired image to satisfy various criteria. If the criteria are satisfied, the trigger event passes the acquired image (which generated the event), or another subsequent image to inspection.

By way of general example, an image-acquisition-based trigger mode as implemented in prior systems typically operates to capture images continuously (meaning in a continuing sequence for some period of time—that sequence potentially skipping frames or acquiring every available frame), while attempting to satisfy a predetermined "trigger logic" (i.e. the rules and criteria that cause a trigger event). This trigger logic is designed to pass when an object enters sufficiently/fully into the vision system's field of view. Once the trigger logic passes, the vision system then transmits the acquired image to another logic process to perform the main inspection and return/output the associated inspection results.

Other potential disadvantages of internal (within the vision system) and external (using a separate camera or other monitoring device) trigger logic using image acquisition is that the acquisition counts between the vision system and external monitoring devices become inaccurate. This can occur, for example when image acquisitions that trigger the trigger logic are not counted as main inspection triggers and theses two counts fall out of synchronization. Also, there are disadvantages resulting from gating of output inspection results (for example via discrete I/O) when running the trigger logic. Other complications can also arise in using an image-acquisition-based trigger logic (e.g. looping, changing trigger modes, and enabling/disabling trigger and inspection logic).

It is therefore desirable to provide a trigger functionality that is readily configurable based on a variety of variable parameters via a user interface. This trigger functionality should avoid common disadvantages of complexity and loss of synchronization with inspection processes.

SUMMARY OF THE INVENTION

This invention overcomes disadvantages of the prior art by providing a user-configurable trigger for a vision system that can be set using a user interface that allows the straightforward variation of a plurality of exposed trigger parameters. Illustratively, the configuration of triggers is performed in a manner similar to the programming of inspection tasks, using the interface. Illustratively, the vision system includes a triggering mode in which the system keeps acquiring (i.e. continuously acquires) images of a field of view with respect to objects in relative motion. The system runs user-configurable "trigger logic". When the trigger logic succeeds/passes, the current image or a newly acquired image is then transmitted to the main inspection logic for processing. As a user-configurable trigger logic, it can be readily configured by a user operating an interface, which can also be used to configure the main inspection process, to trigger the vision system by tools such as presence-absence, edge finding, barcode finding, pattern matching, image thresholding, or any arbitrary combination of tools exposed by the vision system in the interface. Notably, the illustrative embodiments provide the user the ability to arbitrarily configure the trigger logic using the tools exposed by the vision system in an effort to afford the user substantial flexibility to customize trigger criteria to a specific vision system task.

In an illustrative embodiment, a system and method for using a configurable trigger for a vision system includes a vision system camera that acquires images objects moving relative to a field of view of the camera. A vision system interface is constructed and arranged to allow user access to a plurality of vision system tools to process the acquired images. A trigger configuration function resides within the interface, and is constructed and arranged to allow a user to configure at least some of the plurality vision system tools (defined herein to include any available vision system functions) to define a trigger logic by which an event is triggered. A main inspection configuration function also resides within the interface, and is constructed and arranged to allow a user to configure the vision system tools to define a main inspection logic that operates on at least one of the images in response to the triggered event. The trigger configuration can illustratively employ all the tools available to the main inspection configuration function. These functions can be provided in a user-selectable trigger mode interface that includes user-selectable buttons that expose at least some of the plurality of tools. The trigger mode interface further includes a trigger logic dialog screen that displays a trigger logic criteria based on selected ones of the tools. These criteria can include user or machine-defined threshold values and/or pass/fail criteria. Illustratively, the trigger logic operates on a sequence of the acquired images and, when the triggered event occurs, provides at least one image that triggers the event to the main inspection logic. Alternatively, or in addition, the trigger logic can provide an image (or a plurality of images) acquired subsequent to an image that triggers the event. In an embodiment, the sequence of images can be acquired at a higher frame rate and/or lower resolution (or in regions of interest) compared to the image being provided to main inspection after the event is triggered. In this manner triggers can occur at a higher frequency, with reduced processor overhead.

BRIEF DESCRIPTION OF THE DRAWINGS

The invention description below refers to the accompanying drawings, of which.

DETAILED DESCRIPTION

Figure 1:
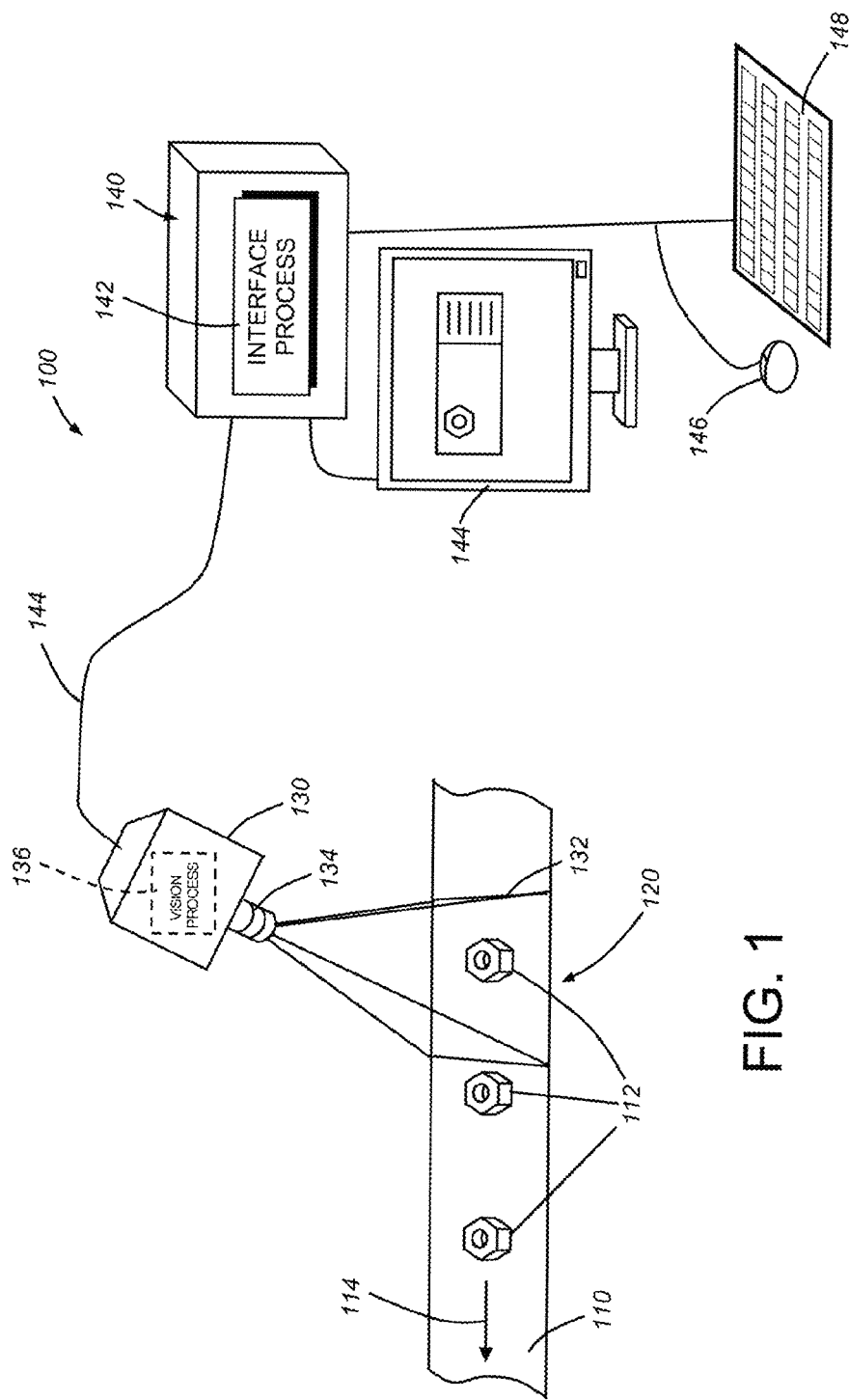
FIG. 1 is a diagram of an exemplary manufacturing arrangement having a moving line with an inspection station including a vision system with a configurable trigger logic according to an illustrative embodiment.

FIG. 1 shows a manufacturing arrangement 100 that includes an exemplary, moving production line 110 that directs a plurality of objects 112 in a direction (arrow 114) though the inspection location 120 at which a vision system camera 130 is positioned. An illuminator (not shown) can be provided to the camera and/or at a location remote from the camera so as to illuminate the field of view 132 at the inspection location. The camera 130 in this embodiment includes an appropriate lens 134, adapted to image the field of view 132 and the object 112 therein with appropriate levels of detail. An appropriate image sensor (not shown) mounted orthogonally to the optical axis within the camera is used to capture the image and convert it to pixel data, typically in grayscale, but optionally in color. The vision system camera 130 can include an on-board vision process/processor (dashed block 136), which performs the system's image acquisition and image processing tasks.

An example of a commercially available vision system with on-board image-processing capability if the In-Sight™ product line from Cognex Corporation of Natick, Mass. Such systems and those of competing vendors provide a programmable camera system that employs an interface to set up particular machine vision tools, functions and/or tasks. The interface is interconnected by a link either on a temporary or full-time basis. In an illustrative embodiment, the interface used for set-up, programming and/or monitoring of the camera 130 is provided on a standalone or networked computer (e.g. PC 140), running an interface process 142. The computer 140 is interconnected to the camera 120 via a wired and/or wireless link 144. Alternatively some or all of the image processing and vision system tasks can be performed within a remote standalone or networked processing system (e.g. PC 140), having an appropriate video acquisition peripheral (e.g. a framegrabber, etc.).

As used herein, and for completeness, the term vision system "tool", shall refer to any configurable application or function that allows a particular aspect of an image to be examined to provide a result in relation to the image. A "tool" as defined herein can be taken to include edge detectors, blob analyzers, calipers, contrast tools, light/dark histogram analysis, flaw detectors, ID (barcode, etc.) readers, pattern matchers and search tools, and any other automated vision system function that allows an image to be examined and reported upon.

In the illustrative embodiment, the computer 140 includes conventional interface devices, such as a display 144, mouse 146 and keyboard 148. This is exemplary of a variety of interface arrangements (e.g. a touch screen), some of which are purpose-built for the particular vision task. Other peripherals and devices, such as robot manipulators and additional vision system cameras can be interconnected with the depicted vision system arrangement 100 according to various embodiments.

Figure 2:
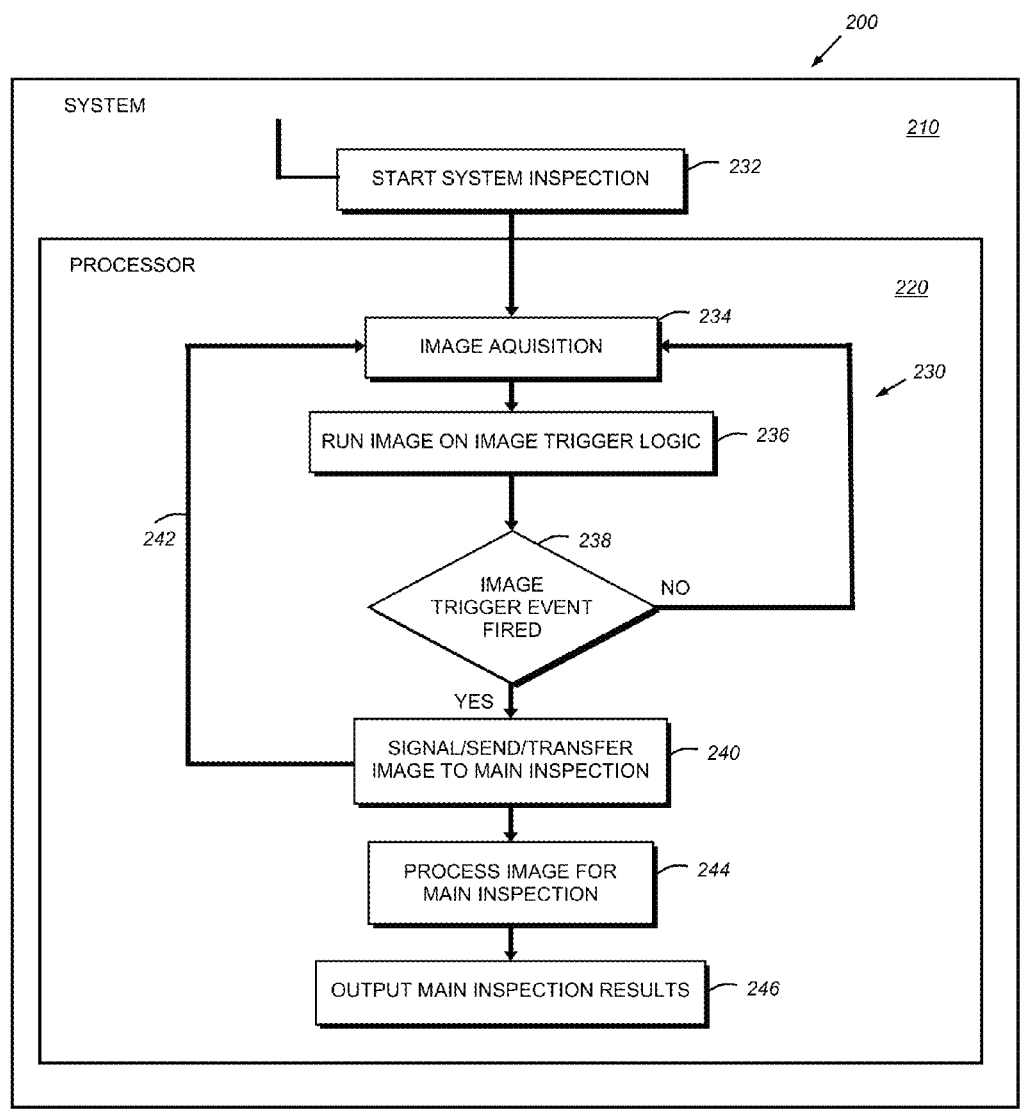
FIG. 2 is a block diagram of a uniprocessor vision system in accordance with FIG. 1 having a single processor that performs a trigger process and an inspection process according to an embodiment.

Reference is now made to FIG. 2, which shows a block diagram 200 of a vision system 210 having a single processor 220 for executing a pre-configured trigger and inspection process 230 according to an illustrative embodiment. This processor can be one or more individual processing chips (e.g. a multi-core processor) on a single die. As described below, the trigger process can alternatively be performed across multiple processors either residing within a single vision system camera/platform or distributed over a plurality of networked vision system cameras/platforms and/or in conjunction other processing devices (e.g. a PC). Illustratively, the depicted process 230 initiates in association with startup of the system (step 232). The process 230 then acquires an initial image of the scene in step 234. This image is analyzed by the configured trigger logic in step 236. If the features within the acquired image do not match the criteria for triggering in decision step 238, then a trigger event has not been fired, and the process 230 branches back to acquisition step 234, continuing to search for a trigger event based on the programmed trigger logic. The previous acquired image is eventually discarded from memory—either immediately or within a predetermined number of subsequent acquisitions. As described below, the programming of the trigger logic can be based upon trained image data (from actual acquired image data or synthetic image data) that operates various tools including blob analysis, edge detectors, and the like. These tools operate in a known manner to identify programmed/trained features within the acquired image. When the features are sufficiently identified, then the process 230 can ensure that an object is sufficiently in the field of view to allow a full inspection of that object, potentially using more robust vision system tools.

In general, the process 230 performs a high-speed continuous loop (for example at a rate of approximately 200 acquisitions per second), passing each acquired image through the trigger logic. When an acquired image satisfies the trigger logic (decision step 238), it (or another newly acquired image in the acquisition sequence) is then passed/transmitted to the main vision system inspection process—or that main vision process is otherwise signaled to access and analyze the stored image (step 240). The process 230, then branches (via procedure branch 242) to continue acquiring images for the next trigger event (step 234), while the triggered sent/accessed image is processed by the main inspection process in step 244. The results of the inspection process (244) are eventually output for use by the overall procedure (step 246). For example, the inspection can indicate a good or flawed part, object alignment data, and/or other useful statistics about an object. The various types of outputs and modalities for displaying and employing output information are known to those of skill. For example, information can be displayed on the camera body or a remote indication as a light (red/green) or sound. Alphanumeric data (e.g. barcode data, alignment data, etc.) can be displayed or stored. Any output information and/or images also can be displayed on an interface display screen via a PC, laptop computer, tablet computer, SmartPhone, and the like. Moreover the output information can be used to drive devices, such as robotic manipulators, defective-part "kickers" or chutes or assembly line shutoffs.

Note that a trigger event need not be based on a single acquired image that passes the trigger logic. In an embodiment a trigger event can require that a predetermined plurality of images pass the trigger logic. This images can be in a continuous sequence or at some other interval with respect to each other. This can ensure that a single image does not generate a trigger event based where there is a possibility of a false reading. In various embodiments acquired at an accelerated frame rate (see below), can enable the use of multiple images to generate a trigger event. Hence, as defined herein, "one or more" images can be employed to generate a trigger event based upon the trigger logic.

It should be noted generally that the quick and robust computational tasks performed in both the trigger process and subsequent main inspection processes are enabled by recent advances in image processing speed brought about by commercially available multi-core processors with high clocking speeds and large online memory capacities. These now-relatively-inexpensive components have made possible the rapid performance of an iterative, high-speed procedures, such as the triggering process described herein. These processes can be performed without compromising the runtime acquisition and manipulation of image data by other functions of the overall vision system.

Figure 3:
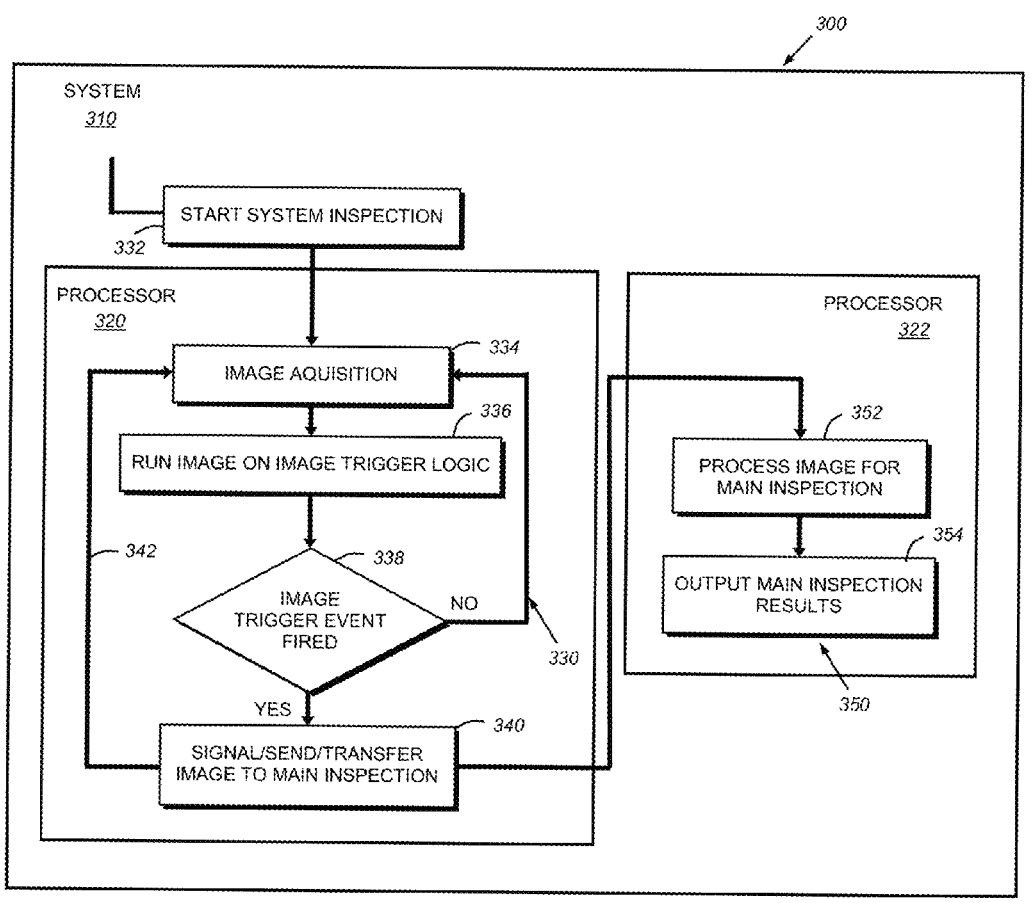
FIG. 3 is a block diagram of a vision system in accordance with FIG. 1 having multiple processors/processor functions that respectively perform the trigger process and the main inspection process according to another embodiment.

Referring to the diagram 300 of FIG. 3 showing an alternate embodiment, the system 310 can employ multiple processors 320 and 322 to perform different portions of the overall trigger and inspection process 330 and 350, respectively. The use of multiple processors 330 and 332 can entail two discrete physical processors on a single die, or on different dies that are interconnected by a communication link. The processors can be part of the same overall device, or can be on different devices (e.g. two interconnected cameras or a camera and a PC). Moreover, the two processors can be "virtual" processor blocks both instantiated within a single-die, physical processor. One example is a multi-thread processor, where each thread is a different processor.

The multi-processor system 310 of FIG. 3 initiates operation of the trigger and inspection processes 330 and 350 at startup (step 332). The trigger process 330, executing on the processor 320, operates generally in a manner described above. That is, images are acquired continuously at high speed (step 334). The trigger logic is applied to each image as it is analyzed by vision system tools (step 336). If the trigger logic criteria are not met, then the process 330 loops back to acquisition step 334 to work on the next acquired image (decision step 338). Conversely, if the acquired image meets the trigger logic criteria, then a trigger event is fired via decision step 338. The process 330 sends acquired image data to, and/or signals access of that data by, the main inspection process 340, while the trigger process 330 branches back top the acquisition step 334 (via branch 342) to work on the next acquired image.

The main inspection process 350 is carried out in the separate processor 322, which receives image data from the acquisition process either directly through access of the system's data memory in response to an appropriate signal (step 340) or via a communication link that transfers the data to the second processor and any associated data memory. When received, the image data is processed by the main inspection process 350 using appropriate vision system tools and techniques (step 352). The results of the inspection are then output in step 354 as described above.

Figure 4:
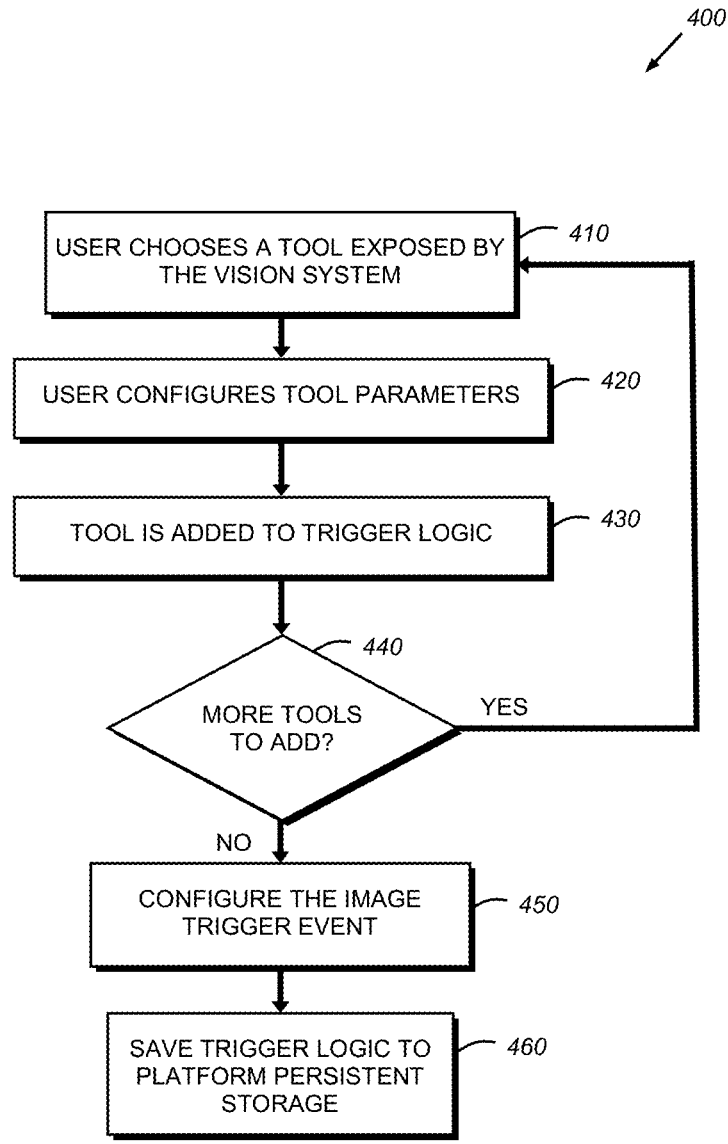
FIG. 4 is a flow diagram of an illustrative user-based trigger logic configuration process for use with the vision system in accordance with FIG. 1.

The ability of a user to configure the parameters or criteria of the trigger logic using various vision system tools exposed in a user interface is highly advantageous to providing a good basis for determining when an appropriate image of an object is acquired and can be inspected successfully. FIG. 4 details a user-based procedure 400 for configuring the trigger logic according to an illustrative embodiment. In step 410 the user enters trigger configuration mode on the interface (a graphical user interface (GUI) described below) to select a given vision system tool, which is exposed as part of a menu of choices. The user then configures the tool's parameters as appropriate to the particular tool in step 420. For example, if the tool is an edge finding tool, the user defines locations of expected edges in a runtime image of the object. In step 430, the configured tool is then added to the trigger logic as part of a list of tools that are applied to each acquired image. In an embodiment, some or all of the vision system tools available in runtime inspection are also available in the image trigger process. Alternatively, the list of tools can be reduced and the tools that run more efficiently can be employed. The tools can operate on the entire image, or on regions of interest within the image. The configuration procedure 400 queries for additional tools (decision step 440). If the user desires to apply further tools (e.g. blob analysis, caliper, etc.), the procedure branches back to the selection step 410. If all tools have been configured and added, then the trigger event is fully configured (step 450). Note, as defined herein the "image trigger event" is the process by which the trigger logic forwards the acquired image to the main inspection. This happens when this event is fired (or signaled) in the trigger logic, which is based on the selected criteria of the user. In step 460, the configured trigger logic is then saved to program memory/data storage associated with the appropriate process of the vision system.

Figure 5:
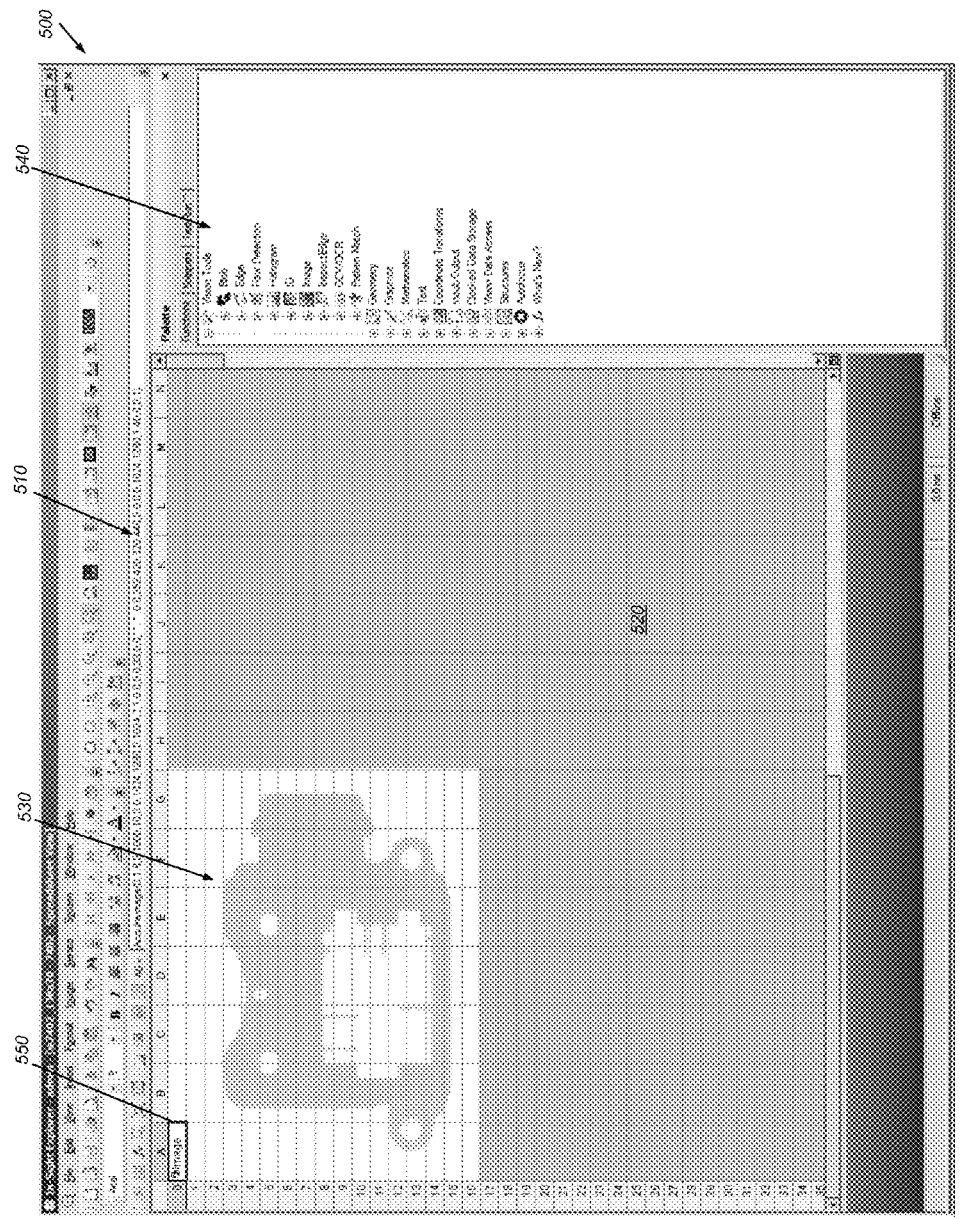
FIG. 5 is a diagram of a graphical user interface (GUI) display of a trigger configuration application for use with the vision system of FIG. 1 in accordance with an illustrative embodiment, showing a main spreadsheet for configuring trigger logic and inspections.

Reference is now made to FIGS. 5-9, which show various screens of a graphical user interface (GUI) display used to configure trigger logic in an illustrative embodiment. This GUI is based upon an exemplary spreadsheet that allows various vision system functions to be configured. An example of such a spreadsheet is employed in connection with the above-described. In-Sight system. However, a variety of alternate GUI styles and arrangements of data and inputs can be used in alternate embodiments—for example a ladder logic-style interface. As shown in FIG. 5, the display 500 provides a main inspection spreadsheet. A trigger mode called "Image" is provided in an illustrative embodiment. This mode provides a mechanism for configuring the image trigger using available vision system tools.

Illustratively, the AcquireImage function is a location in the overall spreadsheet interface in which all other functions reference in order to execute when the vision system acquires an image. This function can not be removed from the spreadsheet 510, and is the location for configuring various acquisition parameters, such as exposure time. The AcquireImage function's property sheet is the location where the acquisition parameters are manipulated and an illustrative location to provide the configurable image trigger. A graphical version of the training image 530 appears in the main window 520 of the spreadsheet 510. A set of available vision tools and vision system processes appears in the side pane menu 540.

Figure 6:
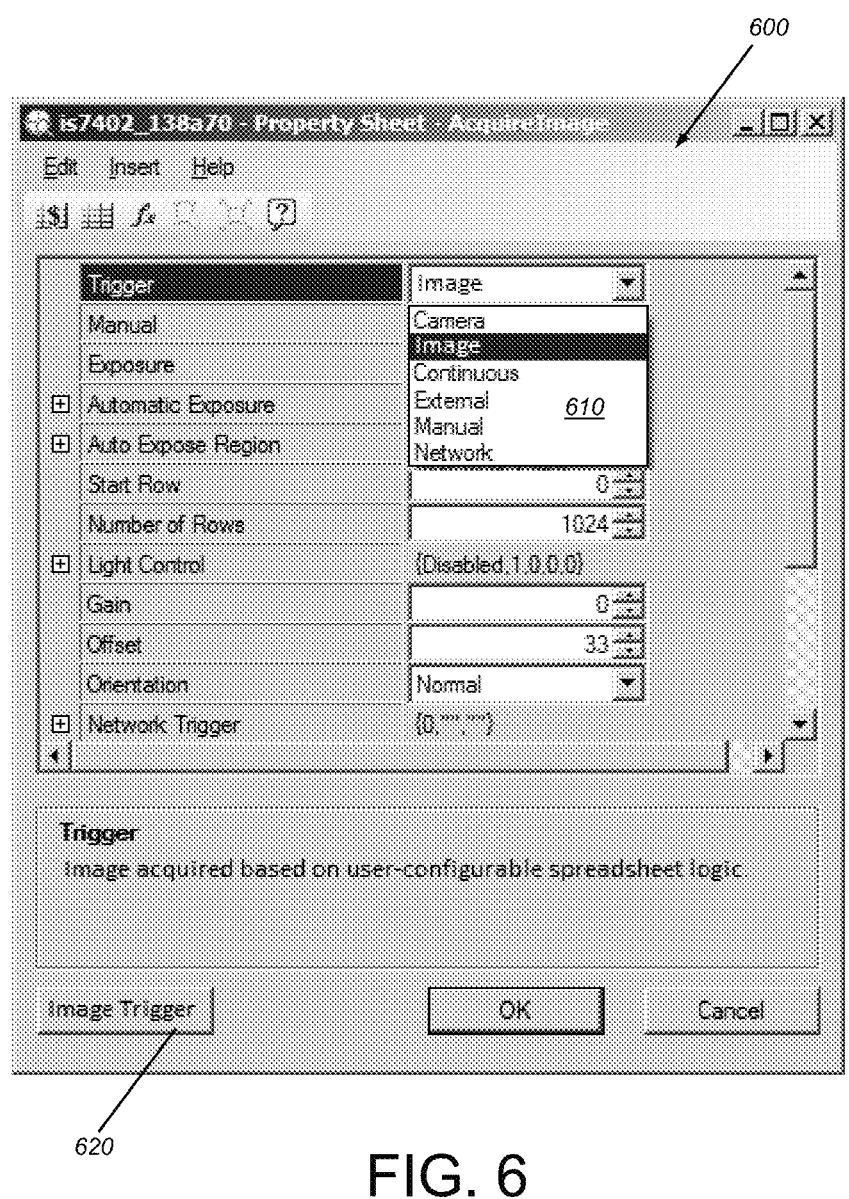
FIG. 6 is a diagram of a vision system trigger properties box for use with the interface of FIG. 5 in which the illustrative image trigger mode with configurable trigger logic is selected.
Figure 7:
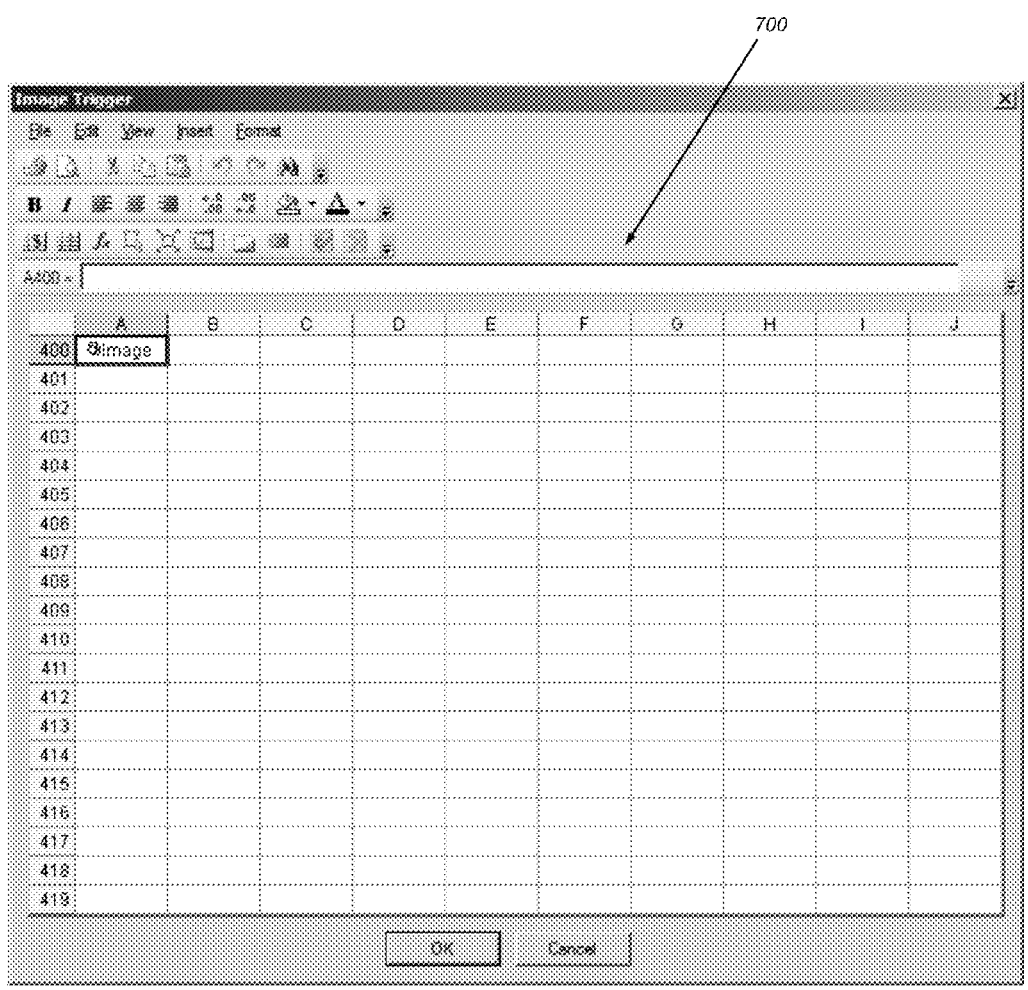
FIG. 7 is an image trigger dialog in the form of a multi-cell spreadsheet for use with the interface of FIG. 5.
Figure 8:
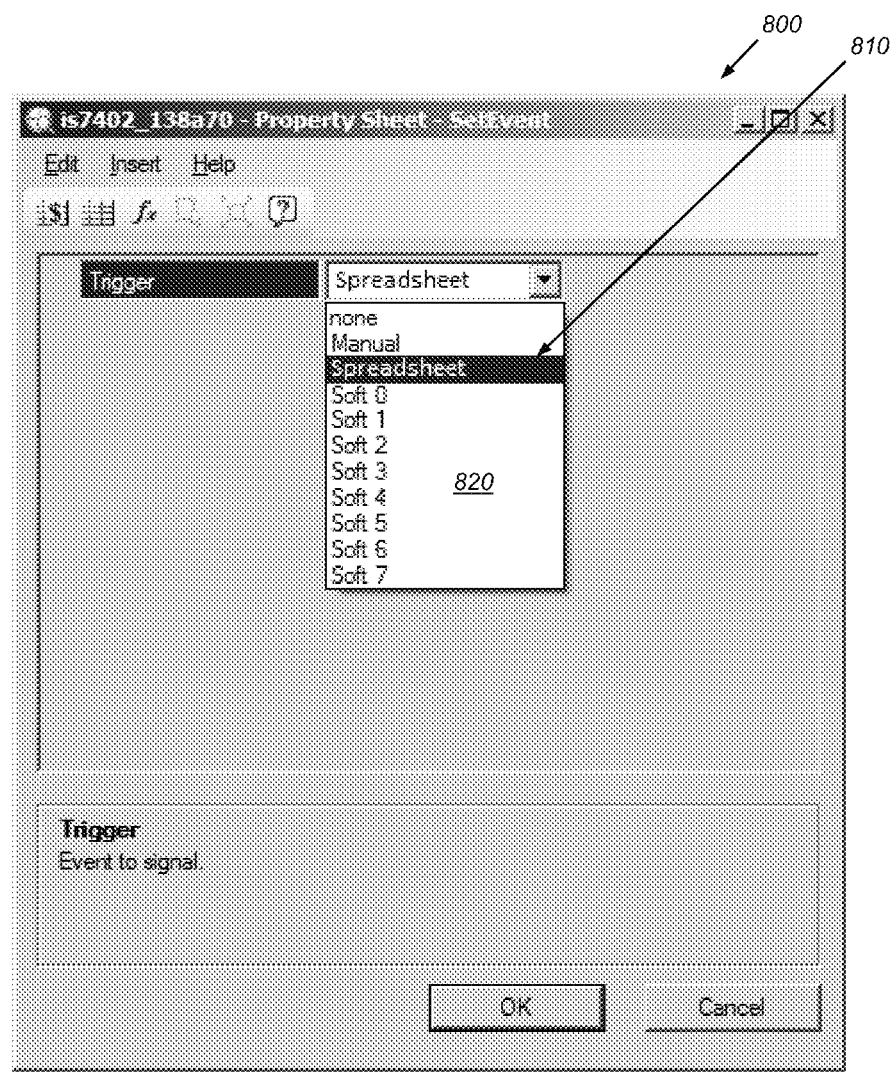
FIG. 8 is a set event property box for use with the interface of FIG. 5, providing a mechanism to signal/set trigger events.
Figure 9:
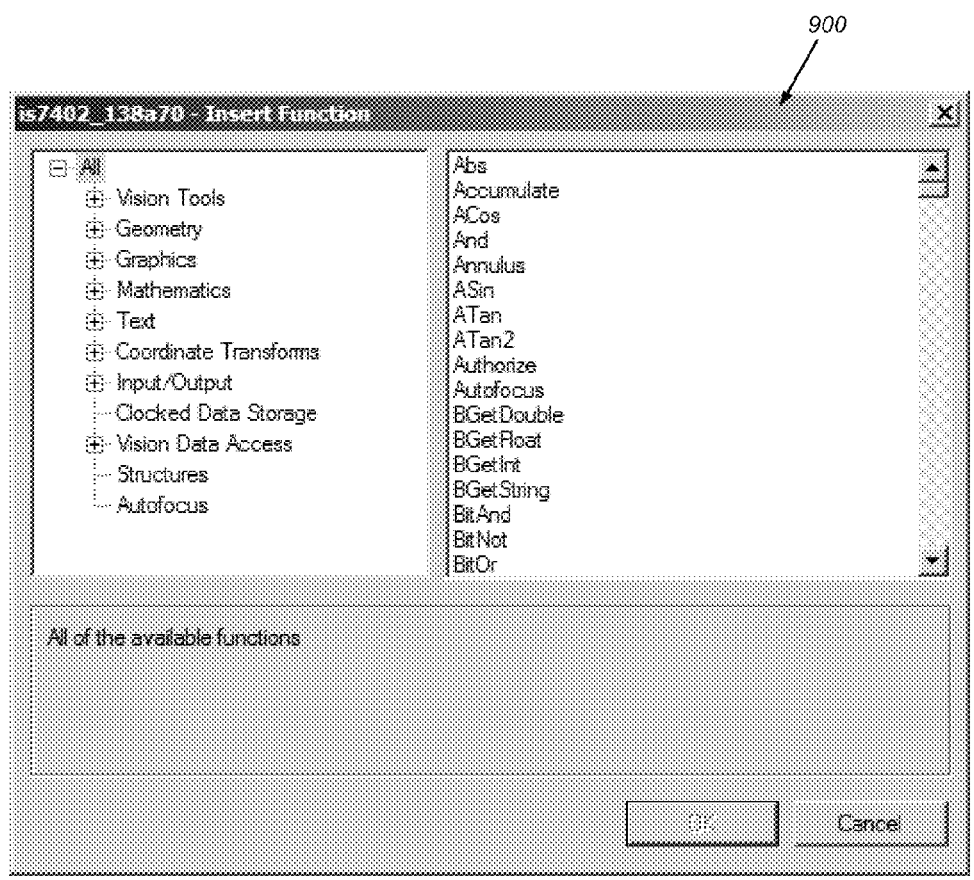
FIG. 9 is a menu box for function selection in providing vision system tools and functions to the trigger logic and main inspection for use with the interface of FIG. 5.
Figure 10:
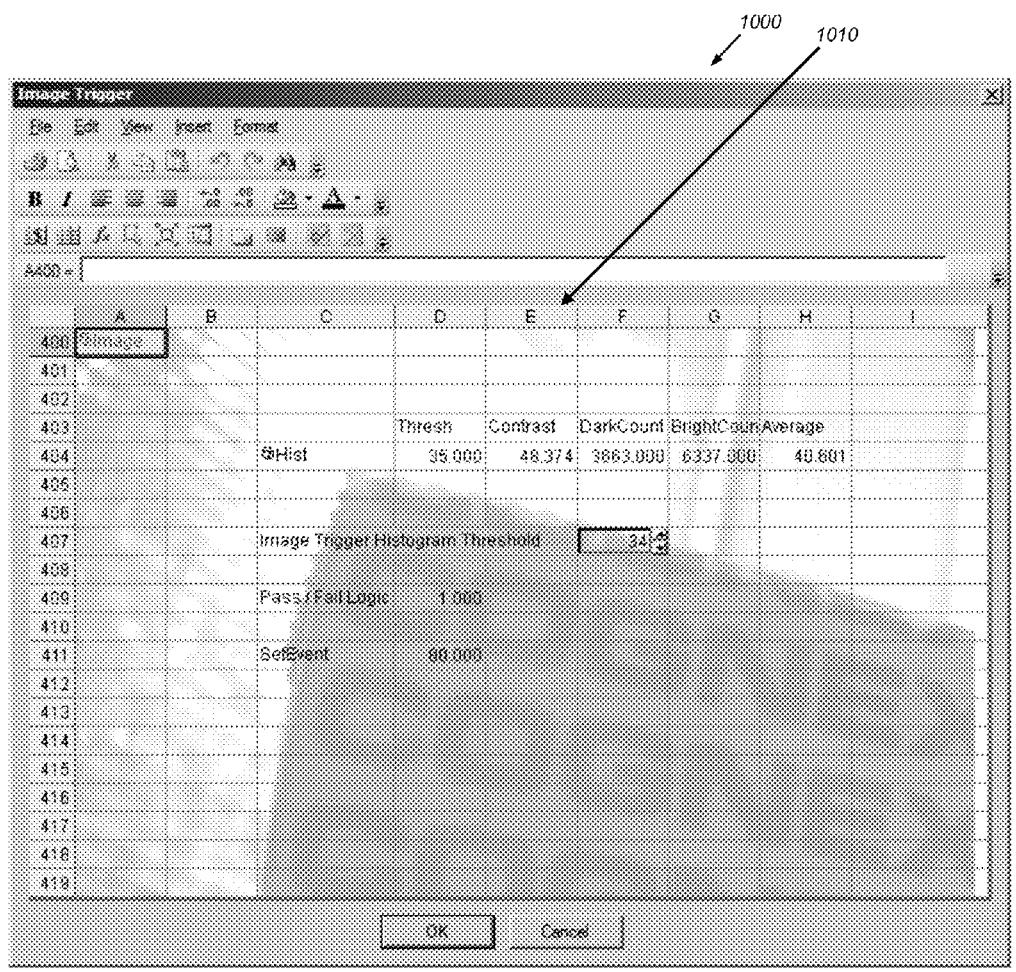
FIG. 10 is an exemplary display of the image trigger dialog of the interface of FIG. 5 programmed to employ a bright/dark histogram analysis to base event triggers.
Figure 11:
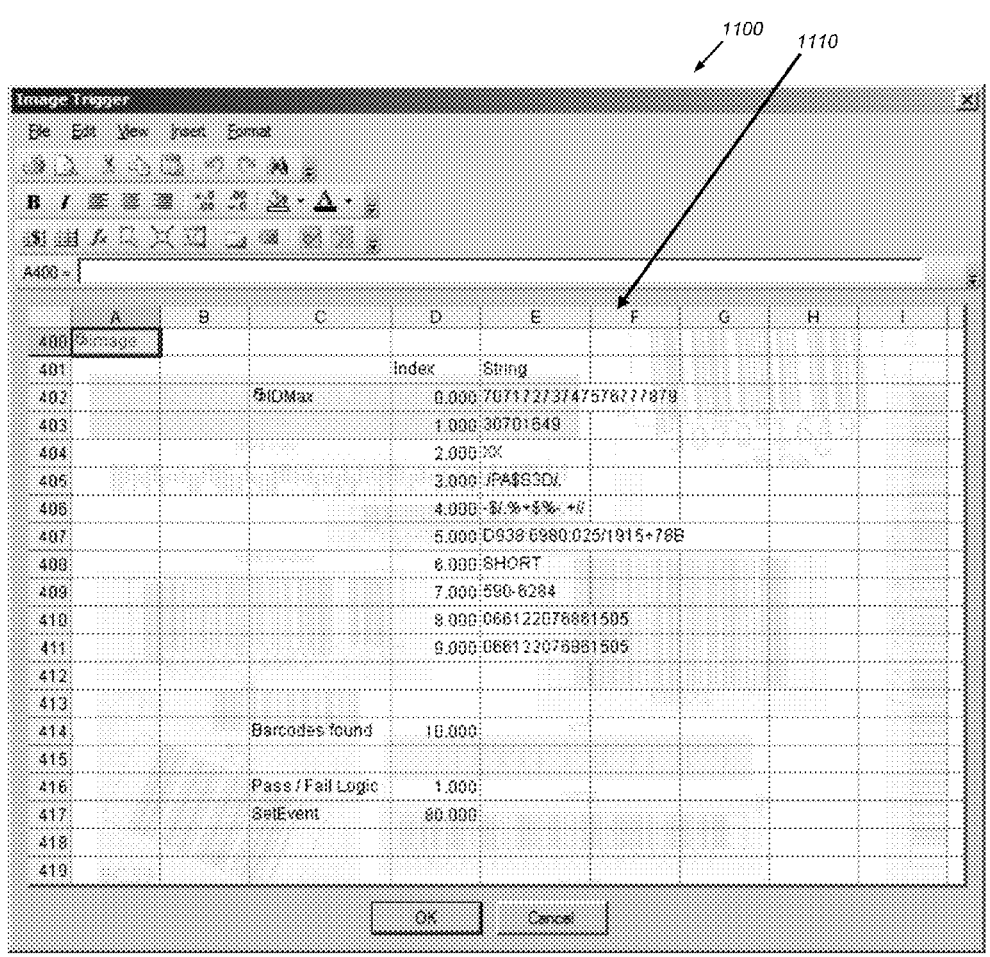
FIG. 11 is an exemplary display of the image trigger dialog of the interface of FIG. 5 programmed to employ an ID/barcode finding function to base event triggers.

With further reference to the Trigger properties box 600 of FIG. 6. The interface illustratively includes a trigger mode called "Image" (box 550 in FIG. 5) that allows analysis of the image in addition to other selectable triggers (e.g. external triggers such as photoeyes, encoders, etc., manual triggers, and the like) to be employed. See dropdown box 610. A button labeled "Image Trigger" 620 can be enabled when this mode is selected. When pressed, the Image Trigger button illustratively launches the Image Trigger dialog window (and associated spreadsheet) which can allow the user to configure the trigger logic. This dialog box is shown in further detail in FIG. 7.

The Image Trigger Dialog window 700 can resemble a typical spreadsheet (the Image Trigger Spreadsheet) with its own AcquireImage function. This AcquireImage function is typically arranged so that it cannot be deleted and is free of input parameters. The AcquireImage function is thus used as an input reference to drive the execution of other functions in the Image Trigger Spreadsheet.

In an illustrative embodiment, Image Trigger dialog 700 includes an Event type (provided in box 800 of FIG. 8) that allows for the use of an interface spreadsheet to trigger the event. Illustratively, events in the exemplary vision system interface arrangement can be used to signal the execution of the main spreadsheet logic. In this case, the illustrative event type called "Spreadsheet" 810 in the associated Trigger dropdown box 820 is used to establish the trigger event. This trigger event is used to execute the main inspection process on the object. The user thereby signals a Spreadsheet Event (using a SetEvent function) based on the logic he or she programmed into the Image Trigger dialog 700. The Spreadsheet Event therefor drives the execution of the main spreadsheet inspection.

As described above, the Image Trigger spreadsheet logic is fully configurable in the illustrative embodiment. The user can utilize all of the vision system's exposed tools or functions to generate events that drive the main inspection spreadsheet. These are provided in the illustrative interface box 900 (FIG. 9), which provides a list of tools and other functions that are exposed by the system and can be inserted into the trigger logic.

The following are examples of the configuration of trigger logic using the illustrative interface. Reference is first made to the display 1000 of an Image Trigger dialog 1010 defining an array of spreadsheet cells. In this example, the Image Trigger dialog has been programmed to signal a Spreadsheet Event when a histogram threshold is above a desired value. In Image Trigger mode, the vision system continuously acquires images and sends them to the Image Trigger spreadsheet for processing. In this example the ExtractHistogram function (cell C404) will execute based on its reference to AcqurieImage (cell A400). Then, the HistThresh function (cell D404) will execute and extract the threshold data from the Hist structure. If the histogram threshold is above the value in F407 then the execution will send a Spreadsheet Event (using the SetEvent in cell C411) to the main inspection for processing of the acquired image. The pass/fail logic in cell D409 compares the histogram threshold with the set input value (e.g. 34) in F407. This spreadsheet 1010 represents the full logic that decides whether or not to signal a Spreadsheet Event, and thus forward the image to the main inspection for processing.

Reference is now made to a display 1100 having an exemplary barcode-reading Image Trigger dialog 1110. The dialog is programmed to signal a Spreadsheet Event when there is a valid barcode (ID) in the field of view. By way of example, the ReadIDMax function (cell C402) is returning up to 10 barcode results. The function GetNumResults (cell D414) is returning the number of barcodes the ReadIDMax function has decoded successfully. The pass/fail logic in cell D416 returns 1 if the ReadIDMax has found at least 1 barcode in its field of view. This is a representation of the full logic that drives the Image Trigger spreadsheet to signal a Spreadsheet Event by executing the SetEvent function (cell D417).

Figure 12:
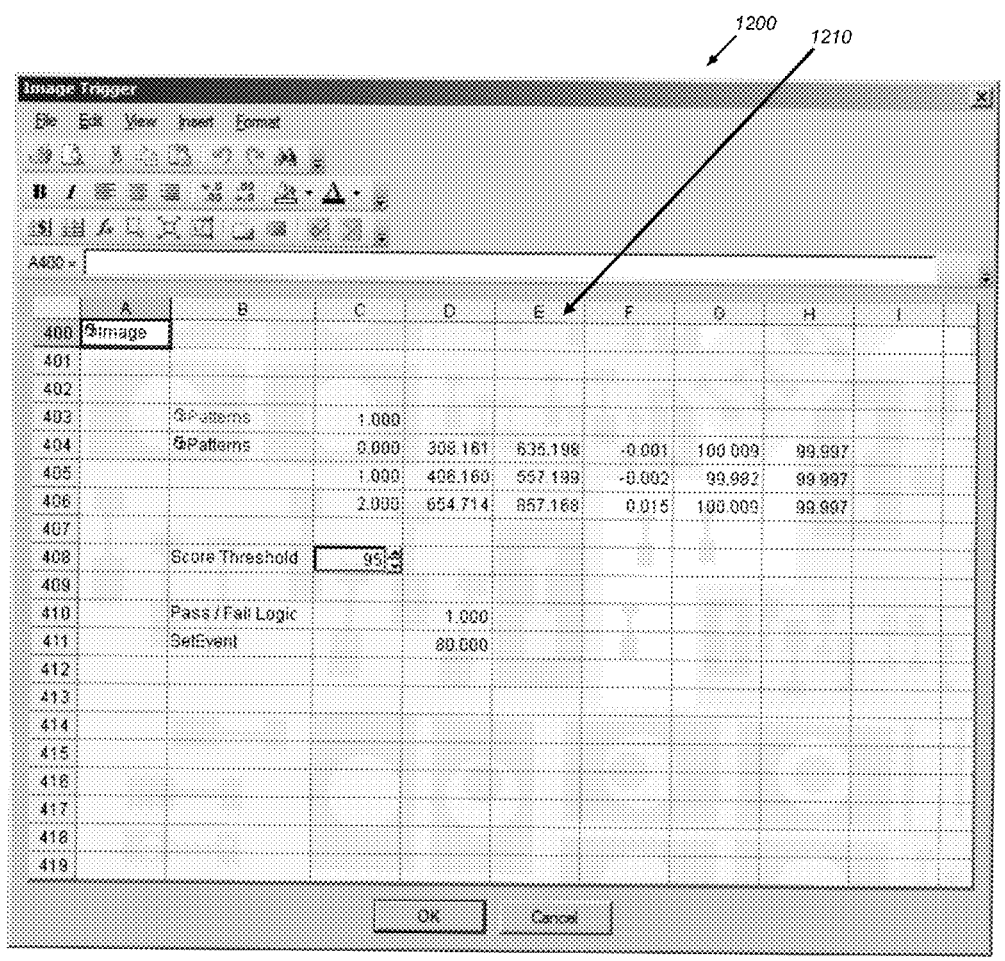
FIG. 12 is an exemplary display of the image trigger dialog of the interface of FIG. 5 programmed to employ pattern recognition/matching relative to training data to base event triggers.

Reference is now made to the exemplary display 1200 of FIG. 12, which shows the Image Trigger spreadsheet 1210 configured for pattern matching of an object. In this example, the Image Trigger dialog is programmed to send a Spreadsheet Event to the main processing spreadsheet based on pattern recognition of an imaged object. The Image Trigger spreadsheet will signal a Spreadsheet Event (cell D411) when it sufficiently matches the pattern which has been trained in cell C403 and is above the desired threshold (cell C408). The pass/fail logic (cell D410) provides a respective I/O value for the Event. In this example, the match of the pattern to the training image is required to score 95/100 to present a pass value.

It should be clear that the above-described examples are only a few of the wide range of possible criteria that can be programmed into the trigger logic. Any appropriate combination of tools and vision system functions can be combined to achieve the specific trigger criteria.

In an embodiment, the image trigger mode can take advantage of capabilities and functions within the camera and acquisition hardware/software that allow for an increased frame rate and/or reduced image resolution to speed acquisition of an event-triggering image. For example, where the camera and acquisition hardware/software allows for binning of sensor rows (of image pixels) or skipping of alternating rows (and/or columns of pixels), the trigger logic can operate on somewhat lower-resolution images to speed the process. The tools used in the logic can be adapted to be less sensitive to a high resolution image. This allows for more acquisitions and trigger logic analysis to occur within a given time frame. If an event is triggered by the trigger logic using lower-resolution, higher frame rate images, then a next acquired image (as soon as the event is recognized and acted upon by the system) can be acquired at a higher resolution, and transmitted to the main inspection logic. This embodiment thus allows the trigger logic to operate more rapidly, thereby allowing objects to pass through the field of view more quickly. Other techniques for increasing frame rate can be implemented in alternate embodiments with the goal of accelerating the triggering of an event, when the object is sufficiently within the field of view.

Illustratively, in programming trigger logic using a reduced frame rate and subsequent, higher resolution image for inspection, the user can configure the appropriate vision tools to identify features that are associated with a leading portion of the object so that a trigger event occurs while the object is just arriving within the field of view. In this manner, the speed of the line can be accelerated while ensuring that the object has not begun to vacate the field of view when the inspection image is actually acquired.

Also illustratively, the interface can include a library of pre-programmed trigger logic configuration templates consisting of tools and appropriate settings/thresholds for the tools. These configurations can be used for commonly encountered trigger and inspection tasks to ease use of the interface in conventional implementations of the vision system. For example, a pre-programmed barcode reader trigger configuration can be employed with, for example 1D and 2D barcodes.

It should be clear that a system and method for configuration of image-acquisition-based trigger logic enables an efficient, versatile and reliable technique for acquiring inspection images when an object is fully within the field of view. The illustrative embodiments herein avoid loss of synchronization and potential errors that can result from employing a separate image-based-trigger or other position sensing device. More particularly, the illustrative embodiments herein allow for trigger logic to be programmed using the same interface and available tools used in main inspection. A wide variety of such tools are made available, ensuring that the trigger logic can achieve a positive result.

The foregoing has been a detailed description of illustrative embodiments of the invention. Various modifications and additions can be made without departing from the spirit and scope of this invention. Each of the various embodiments described above may be combined with other described embodiments in order to provide multiple features. Furthermore, while the foregoing describes a number of separate embodiments of the apparatus and method of the present invention, what has been described herein is merely illustrative of the application of the principles of the present invention. For example, while a moving line with objects that pass under a stationary inspection station is shown, it is expressly contemplated that the station can move over an object or surface or that both the station and objects can be in motion. Thus, taken broadly the objects and the inspection station are in "relative" motion with respect to each other. Also, while the above-described "interface" (also termed a "vision system interface") is shown as a single application consisting of a plurality of interface screen displays for configuration of both trigger logic and main inspection processes, it is expressly contemplated that the trigger logic or other vision system functions can be configured using a separate application and/or a single or set of interface screens that are accessed and manipulated by a user separately from the inspection interface. The term "interface" should be taken broadly to include a plurality of separate applications or interface screen sets. In addition, while the vision system typically performs trigger logic with respect to objects in relative motion with respect to the field of view, the objects can be substantially stationary with respect to the field of view (for example, stopping in the filed of view). Likewise, the term "screen" as used herein can refer to the image presented to a user which allows one or more functions to be performed and/or information related to the vision system and objects to be displayed. For example a screen can be a GUI window, a drop-down box, a control panel and the like. It should also be clear that the various interface functions and vision system operations described herein controlled by these functions can be programmed using conventional programming techniques known to those of ordinary skill to achieve the above-described, novel trigger mode and functions provided thereby. Accordingly, this description is meant to be taken only by way of example, and not to otherwise limit the scope of this invention.

What is claimed is:

1. A configurable trigger for a vision system having a vision system camera that acquires images of objects moving relative to a field of view of the camera comprising:
   a vision system interface constructed and arranged to allow user access to a plurality of vision system tools to process the acquired images;
   a trigger configuration function within the interface constructed and arranged to allow a user to configure at least some of the plurality of vision system tools to define a trigger logic by which an event is triggered when at least one of the acquired images matches a predetermined trigger criteria; and
   a main inspection configuration function within the interface constructed and arranged to allow a user to configure the vision system tools to define a main inspection logic that operates on the at least one of the acquired images and inspects the at least one of the acquired images that matches the predetermined trigger criteria to provide an inspection result in response to the triggered event.

2. The configurable trigger as set forth in claim 1 wherein the interface is constructed and arranged to allow a user to configure all of the plurality of vision system tools.

3. The configurable trigger as set forth in claim 1 wherein the vision system interface is constructed and arranged to provide a user-selectable trigger mode interface, the trigger mode interface including user-selectable buttons that expose at least some of the plurality of tools.

4. The configurable trigger as set forth in claim 3 wherein the trigger mode interface further comprises a trigger logic dialog screen that displays a trigger logic criteria based on selected ones of the tools.

5. The configurable trigger as set forth in claim 4 wherein the criteria include at least one of threshold values and pass/fail parameters.

6. The configurable trigger as set forth in claim 1 wherein the trigger logic operates on a sequence of the acquired images and, when the triggered event occurs, provides the image that triggers the event to the main inspection logic.

7. The configurable trigger as set forth in claim 1 wherein the trigger logic operate on a sequence of the acquired images and, when the triggered event occurs, provides to the main inspection logic an image acquired subsequent to the image that triggers the event.

8. The configurable trigger as set forth in claim 7 wherein the sequence of images is acquired at a frame rate that is higher than a frame rate at which the image acquired subsequent is acquired.

9. The configurable trigger as set forth in claim 7 wherein the sequence of images is acquired at a resolution that is lower than a resolution of the image acquired subsequent.

10. The configurable trigger as set forth in claim 1 wherein the main inspection logic is distinct from the trigger logic.

11. A method for configuring a trigger event in a vision system having a vision system camera that acquires images objects moving relative to a field of view of the camera comprising the steps of:
   operating a vision system interface including a plurality of vision system tools to process the acquired images;
   configuring, with a trigger configuration function within the interface, at least some of the plurality of vision system tools to define a trigger logic by which an event is triggered when at least one of the acquired images matches a predetermined trigger criteria; and
   configuring, with a main inspection configuration within the interface, the vision system tools to define a main inspection logic that operates on the at least one of the acquired images and inspects the at least one of the acquired images that matches the predetermined trigger criteria to provide an inspection result in response to the triggered event.

12. The method as set forth in claim 11 wherein the step of configuring at least some of the plurality of vision system tools to define the trigger logic includes configuring all of the plurality vision system tools.

13. The method as set forth in claim 11 wherein the vision system interface is constructed and arranged to provide a user-selectable trigger mode interface, and wherein the step of configuring at least some of the plurality of vision system tools to define the trigger logic includes accessing on the trigger mode interface user-selectable buttons that expose at least some of the plurality of tools.

14. The method as set forth in claim 13 wherein the step of configuring at least some of the plurality of vision system tools to define the trigger logic includes accessing a trigger logic dialog screen that displays a trigger logic criteria based on selected ones of the tools.

15. The method as set forth in claim 14 further comprising setting the criteria to include at least one of threshold values and pass/fail parameters.

16. The method as set forth in claim 11 wherein the trigger logic operates on a sequence of the acquired images and, when the triggered event occurs, provides the image that triggers the event to the main inspection logic.

17. The method as set forth in claim 11 wherein the trigger logic operates on a sequence of the acquired images and, when the triggered event occurs, provides to the main inspection logic an image acquired subsequent to the image that triggers the event.

18. The method as set forth in claim 17 wherein the sequence of images is acquired at a frame rate that is higher than a frame rate at which the image acquired subsequent is acquired.

19. The method as set forth in claim 17 wherein the sequence of images is acquired at a resolution that is lower than a resolution of the image acquired subsequent.

20. A method for triggering an event in a vision system having a vision system camera that acquires images of objects moving relative to a field of view of the camera comprising the steps of:
   continuously acquiring images within the field of view and analyzing acquired image data from the images;
   applying a pre-configured trigger logic based on at least one of a plurality of user configured vision system tools to the image data from the images;
   when the pre-configured trigger logic achieves a passing result on the image data, providing an event trigger; and
   providing image data to a main inspection logic that operates on the image data and inspects the image data that achieves the passing result to provide an inspection result in response to the event trigger.

* * * * *